(12) United States Patent
Tang et al.

(10) Patent No.: US 10,329,261 B1
(45) Date of Patent: Jun. 25, 2019

(54) METHOD OF PREPARING 6-CHLORO-5-NITRO-2,4-DIAMINOPYRIMIDINE AND ITS APPLICATION THEREOF

(71) Applicant: XI'AN TAIKOMED PHARMACEUTICAL TECHNOLOGY CO., LTD., Xi'an (CN)

(72) Inventors: Yonghong Tang, Xi'an (CN); Minghui Chang, Xi'an (CN); Chengyuan Liang, Xi'an (CN); Danni Tian, Xi'an (CN); Juan Xia, Xi'an (CN); Kaiqi Shi, Xi'an (CN); Han Li, Xi'an (CN); Xuechuan Wang, Xi'an (CN)

(73) Assignee: XI'AN TAIKOMED PHARMACEUTICAL TECHNOLOGY CO., LTD., Xi'an (CN)

( * ) Notice: Subject to any disclaimer, the term of this patent is extended or adjusted under 35 U.S.C. 154(b) by 0 days.

(21) Appl. No.: 16/038,407

(22) Filed: Jul. 18, 2018

(30) Foreign Application Priority Data

Jul. 2, 2018 (CN) .......................... 2018 1 0710221

(51) Int. Cl.
*C07D 239/50* (2006.01)
*A61P 35/02* (2006.01)

(52) U.S. Cl.
CPC ............ *C07D 239/50* (2013.01); *A61P 35/02* (2018.01); *C07B 2200/13* (2013.01)

(58) Field of Classification Search
CPC .................................................. C07D 239/50
See application file for complete search history.

(56) References Cited

U.S. PATENT DOCUMENTS

| 5,863,924 A * | 1/1999 | Berger | ................ | C07D 239/42 514/275 |
| 5,952,331 A * | 9/1999 | Berger | ................ | C07D 239/42 514/256 |
| 2007/0066612 A1* | 3/2007 | Khanzhin | ............ | C07D 239/48 514/235.5 |

OTHER PUBLICATIONS

Marchetti et al. Org. Biomol. Chem. 2010, 8, 2397-2407. (Year: 2010).*
O'Brien t al. J. Med. Chem. 1966, 9, 573-575. (Year: 1966).*
O'Brien et al. J. Med. Chem. 1963, 6, 467-471. (Year: 1963).*

* cited by examiner

*Primary Examiner* — Amanda L Aguirre

(57) ABSTRACT

A method of preparing 6-chloro-5-nitro-2,4-diaminopyrimidine includes: reacting guanidine hydrochloride with ethyl carbamoylacetate and sodium hypochlorite in the presence of a metal nitrate salt and acetate anhydride in an organic solvent.

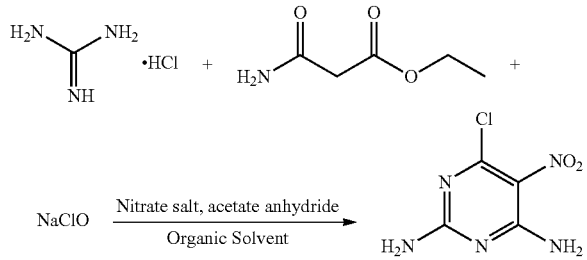

13 Claims, No Drawings

METHOD OF PREPARING 6-CHLORO-5-NITRO-2,4-DIAMINOPYRIMIDINE AND ITS APPLICATION THEREOF

The present invention claims priority to Chinese Patent Application No. 201810710221.6, filed on Jul. 2, 2018, which is incorporated by reference for all purposes as if fully set forth herein.

BACKGROUND OF THE INVENTION

Field of the Invention

The present invention relates to the field of pharmaceutical chemistry, and more particularly, to a method of preparing 6-chloro-5-nitro-2,4-diaminopyrimidine and its application in manufacturing chronic myelogenous leukemia drugs.

Discussion of the Related Art

Leukemia is a collective term for a group of cancer types that usually develop in the bone marrow, causing massive proliferation of abnormal white blood cells. These abnormally increased white blood cells have not yet been developed and are known as bud cells or leukemia cells. Chronic Myeloid Leukemia (CML) is caused by a chromosomal translocation from the Philadelphia chromosome, where the long arm of chromosome 9 moves to the short arm of chromosome 22. CML accounts for about 15% of leukemia. Currently, targeted therapies, such as imatinib, dasatinib, and nilotinib, are mainly used for CML. With the introduction of tyrosine kinase inhibitors (TKI), more patients with CML benefit from the TKI, and their quality of life improves significantly. These drugs, however, still have problems, such as toxic and side effects, intolerance, drug resistance, disease progression, relapse and withdrawal. Therefore, there is still a need for safe and effective CML drugs 6-Chloro-5-nitro-2,4-diaminopyrimidine has a pyrimidine scafold, and is a commonly used intermediate compound. U.S. Pat. No. 5,863,924 discloses aryl pyrimidine derivatives with the following structure as 5-HT2B receptor antagonists.

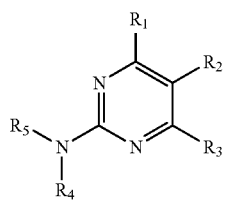

There is no report on aryl pyrimidine derivatives for CML treatment. The present invention discovered for the first time that 6-chloro-5-nitro-2,4-diaminopyrimidine has excellent efficacy in treating CML and can be used for the preparation of a medicament for treating CML.

SUMMARY OF THE INVENTION

In one embodiment, the present invention provides a method of preparing 6-chloro-5-nitro-2,4-diaminopyrimidine. The method includes: reacting guanidine hydrochloride with ethyl carbamoylacetate and sodium hypochlorite in the presence of a metal nitrate salt and acetate anhydride in an organic solvent.

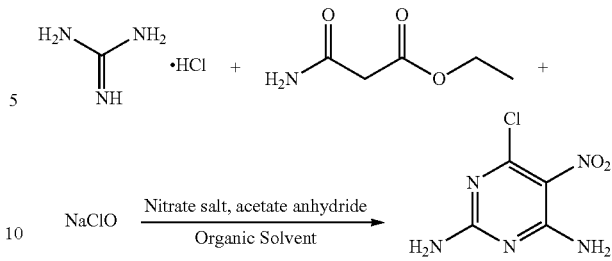

In another embodiment, the reaction of guanidine hydrochloride, ethyl carbamoylacetate, and sodium hypochlorite is a one pot reaction.

In another embodiment, the reaction of guanidine hydrochloride, ethyl carbamoylacetate, and sodium hypochlorite includes the following steps: (1) adding an acidic agent to a mixture of guanidine hydrochloride and ethyl carbamoylacetate in the organic solvent to a pH of 5.0-5.5, heating the mixture to 60-80° C. for 10-12 hours; (2) adding sodium hypochlorite to the mixture, continuing heating the mixture to 60-80° C. for 2-3 hours; (3) cooling the mixture to room temperature, adding the metal nitrate salt and acetate anhydride to the mixture in the presence of an ice water cooling bath, stirring the mixture for 30-40 minutes; (4) cooling the mixture to room temperature, removing the solvent, filtering, washing with ethanol to obtain crude 6-chloro-5-nitro-2,4-diaminopyrimidine; and (5) recrystallizing the crude 6-chloro-5-nitro-2,4-diaminopyrimidine in ethanol to obtain 6-chloro-5-nitro-2,4-diaminopyrimidine.

In another embodiment, the metal nitrate salt is potassium nitrate or copper nitrate trihydrate.

In another embodiment, the organic solvent is ethanol, acetonitrile, or isopropanol.

In another embodiment, the organic solvent is ethanol.

In another embodiment, the molar ratio of guanidine hydrochloride and ethyl carbamoylacetate is 1: 1-1:1.5.

In another embodiment, the molar ratio of guanidine hydrochloride and ethyl carbamoylacetate is 1:1.2.

In another embodiment, the acidic agent is $ZnCl_2$, $AlCl_3$, HCl, or acetic acid.

In another embodiment, the acidic agent is acetic acid.

In another embodiment, in step (2), the mixture is heated to 65° C. for 2 hours.

In another embodiment, the molar ratio of the metal nitrate salt and acetate anhydride is 5:1.

In another embodiment, in step (3), the mixture is stirred for 30 minutes.

In one embodiment, the present invention provides a method of treating chronic myelocytic leukemia in a subject. The method includes providing a therapeutically effective amount of 6-chloro-5-nitro-2,4-diaminopyrimidine; and contacting the subject with the therapeutically effective amount of 6-chloro-5-nitro-2,4-diaminopyrimidine.

In another embodiment, 6-chloro-5-nitro-2,4-diaminopyrimidine inhibits K-562 cells in the subject.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention. These examples are for illustrative purposes only and do not limit the scope or spirit of the invention.

EXAMPLE 1

Preparation of
6-chloro-5-nitro-2,4-diaminopyrimidine

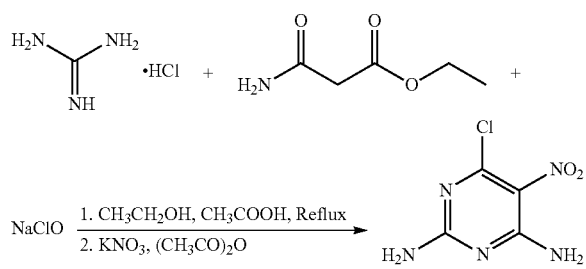

A mixture of 100 mg (1.04 mmol) guanidine hydrochloride, 164 mg (1.25 mmol) ethyl carbamoylacetate (a molar ratio of guanidine hydrochloride and ethyl carbamoylacetate being 1:1.2), and 45 mL ethanol was added to a 100 mL flask. Acetic acid was added slowly to the mixture to a pH of about 5 under stirring, and the mixture was heated at 65° C. for 12 hours. 37 mg NaClO (0.50 mmol) was then added to the mixture, and the mixture was continued to heat at 65° C. for 2 hours. The mixture was cooled to room temperature, and 162 mg (1.51 mmol) potassium nitrate and 31 mg (0.31 mmol) acetic anhydride (a molar ratio of potassium nitrate and acetic anhydride being 5:1) were added to the mixture under an ice water bath. The mixture was stirred under the ice water bath for 30 minutes. The reaction was monitored by thin layer chromatography. When the reaction was complete, the solvent in the mixture was removed under reduced pressure. The mixture was then filtered, washed with ethanol to give a crude product. The crude product was recrystallized in 40 mL ethanol to give 125.1 mg (0.66 mmol) 6-chloro-5-nitro-2,4-diaminopyrimidine, a yield of 63.5%.

6-Chloro-5-nitro-2,4-diaminopyrimidine: $^1$H-NMR (300 MHz, DMSO-$d_6$) δ (ppm): 8.65 (2H, s), 6.42 (2H, s); $^{13}$C-NMR (75 MHz, DMSO-$d_6$) δ (ppm): 170.1, 155.8, 114.3, 130.2; MS (ESI) for (M+H)$^+$: 190.0.

EXAMPLE 2

Preparation of
6-chloro-5-nitro-2,4-diaminopyrimidine

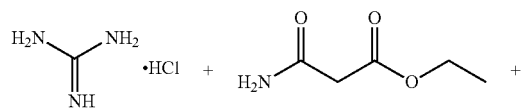

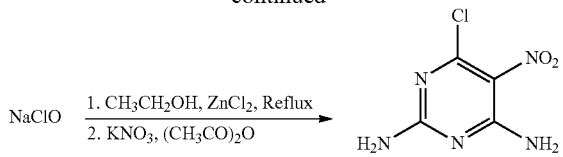

A mixture of 100 mg (1.04 mmol) guanidine hydrochloride, 164 mg (1.25 mmol) ethyl carbamoylacetate (a molar ratio of guanidine hydrochloride and ethyl carbamoylacetate being 1:1.2), and 45 mL ethanol was added to a 100 mL flask. An appropriate amount of zinc chloride (solid) was added slowly to the mixture to a pH of about 5 under stirring, and the mixture was heated at 65° C. for 12 hours. 37 mg NaClO (0.50 mmol) was then added to the mixture, and the mixture was continued to heat at 65° C. for 2 hours. The mixture was cooled to room temperature, and 162 mg (1.51 mmol) potassium nitrate and 31 mg (0.31 mmol) acetic anhydride (a molar ratio of potassium nitrate and acetic anhydride being 5:1) were added to the mixture under an ice water bath. The mixture was stirred under the ice water bath for 30 minutes. The reaction was monitored by thin layer chromatography. When the reaction was complete, the solvent in the mixture was removed under reduced pressure. The mixture was then filtered, washed with ethanol to give a crude product. The crude product was recrystallized in 40 mL ethanol to give 92.8 mg (0.49 mmol) 6-chloro-5-nitro-2,4-diaminopyrimidine, a yield of 47.5%.

EXAMPLE 3

Preparation of
6-chloro-5-nitro-2,4-diaminopyrimidine

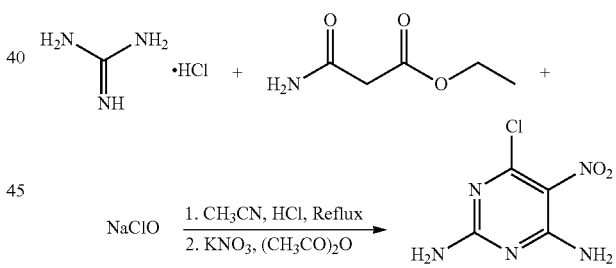

A mixture of 80 mg (0.84 mmol) guanidine hydrochloride, 132.4 mg (1.01 mmol) ethyl carbamoylacetate (a molar ratio of guanidine hydrochloride and ethyl carbamoylacetate being 1:1.2), and 40 mL acetonitrile was added to a 100 mL flask. Hydrochloric acid was added slowly to the mixture to a pH of about 5 under stirring, and the mixture was heated at 65° C. for 12 hours. 29 mg (0.40 mmol) NaClO was then added to the mixture, and the mixture was continued to heat at 65° C. for 2 hours. The mixture was cooled to room temperature, and 93 mg (0.92 mmol) potassium nitrate and 18 mg (0.18 mmol) acetic anhydride (a molar ratio of potassium nitrate and acetic anhydride being 5:1) were added to the mixture under an ice water bath. The mixture was stirred under the ice water bath for 30 minutes. The reaction was monitored by thin layer chromatography. When the reaction was complete, the solvent in the mixture was removed under reduced pressure. The mixture was then filtered, washed with ethanol to give a crude product. The crude product was recrystallized in 35 mL ethanol to give 87.2 mg (0.46 mmol) 6-chloro-5-nitro-2,4-diaminopyrimidine, a yield of 54.8%.

EXAMPLE 4

Preparation of 6-chloro-5-nitro-2,4-diaminopyrimidine

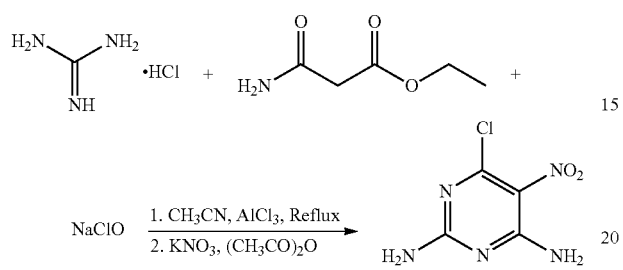

A mixture of 80 mg (0.84 mmol) guanidine hydrochloride, 132.4 mg (1.01 mmol) ethyl carbamoylacetate (a molar ratio of guanidine hydrochloride and ethyl carbamoylacetate being 1:1.2), and 40 mL acetonitrile was added to a 100 mL flask. An appropriate amount of aluminum chloride was added slowly to the mixture to a pH of about 5 under stirring, and the mixture was heated at 65° C. for 12 hours. 29 mg (0.40 mmol) NaClO was then added to the mixture, and the mixture was continued to heat at 65° C. for 2 hours. The mixture was cooled to room temperature, and 93 mg (0.92 mmol) potassium nitrate and 18 mg (0.18 mmol) acetic anhydride (a molar ratio of potassium nitrate and acetic anhydride being 5:1) were added to the mixture under an ice water bath. The mixture was stirred under the ice water bath for 30 minutes. The reaction was monitored by thin layer chromatography. When the reaction was complete, the solvent in the mixture was removed under reduced pressure. The mixture was then filtered, washed with ethanol to give a crude product. The crude product was recrystallized in 35 mL ethanol to give 79.6 mg (0.42 mmol) 6-chloro-5-nitro-2,4-diaminopyrimidine, a yield of 50.4%.

EXAMPLE 5

Preparation of 6-chloro-5-nitro-2,4-diaminopyrimidine

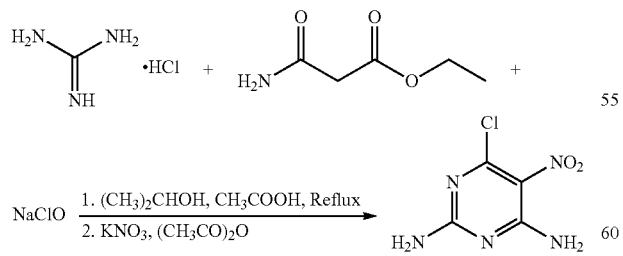

A mixture of 100 mg (1.04 mmol) guanidine hydrochloride, 164 mg (1.25 mmol) ethyl carbamoylacetate (a molar ratio of guanidine hydrochloride and ethyl carbamoylacetate being 1:1.2), and 45 mL isopropanol was added to a 100 mL flask. Acetic acid was added slowly to the mixture to a pH of about 5 under stirring, and the mixture was heated at 65° C. for 12 hours. 37 mg NaClO (0.50 mmol) was then added to the mixture, and the mixture was continued to heat at 65° C. for 2 hours. The mixture was cooled to room temperature, and 162 mg (1.51 mmol) potassium nitrate and 31 mg (0.31 mmol) acetic anhydride (a molar ratio of potassium nitrate and acetic anhydride being 5:1) were added to the mixture under an ice water bath. The mixture was stirred under the ice water bath for 30 minutes. The reaction was monitored by thin layer chromatography. When the reaction was complete, the solvent in the mixture was removed under reduced pressure. The mixture was then filtered, washed with ethanol to give a crude product. The crude product was recrystallized in 40 mL ethanol to give 102.4 mg (0.54 mmol) 6-chloro-5-nitro-2,4-diaminopyrimidine, a yield of 51.7%.

EXAMPLE 6

Preparation of 6-chloro-5-nitro-2,4-diaminopyrimidine

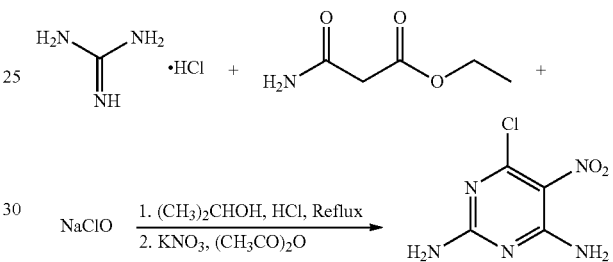

A mixture of 100 mg (1.04 mmol) guanidine hydrochloride, 164 mg (1.25 mmol) ethyl carbamoylacetate (a molar ratio of guanidine hydrochloride and ethyl carbamoylacetate being 1:1.2), and 45 mL isopropanol was added to a 100 mL flask. Hydrochloric acid was added slowly to the mixture to a pH of about 5 under stirring, and the mixture was heated at 65° C. for 12 hours. 37 mg NaClO (0.50 mmol) was then added to the mixture, and the mixture was continued to heat at 65° C. for 2 hours. The mixture was cooled to room temperature, and 162 mg (1.51 mmol) potassium nitrate and 31 mg (0.31 mmol) acetic anhydride (a molar ratio of potassium nitrate and acetic anhydride being 5:1) were added to the mixture under an ice water bath. The mixture was stirred under the ice water bath for 30 minutes. The reaction was monitored by thin layer chromatography. When the reaction was complete, the solvent in the mixture was removed under reduced pressure. The mixture was then filtered, washed with ethanol to give a crude product. The crude product was recrystallized in 40 mL ethanol to give 94.8 mg (0.50 mmol) 6-chloro-5-nitro-2,4-diaminopyrimidine, a yield of 48.3%.

EXAMPLE 7

Preparation of 6-chloro-5-nitro-2,4-diaminopyrimidine

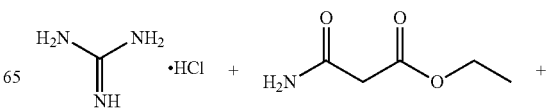

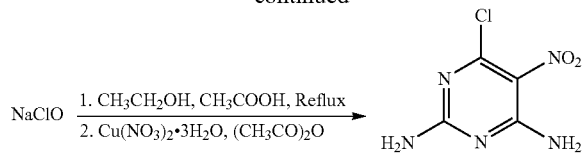

A mixture of 100 mg (1.04 mmol) guanidine hydrochloride, 164 mg (1.25 mmol) ethyl carbamoylacetate (a molar ratio of guanidine hydrochloride and ethyl carbamoylacetate being 1:1.2), and 100 mL ethanol was added to a 250 mL flask. Acetic acid was added slowly to the mixture to a pH of about 5 under stirring, and the mixture was heated at 65° C. for 12 hours. 37 mg NaClO (0.50 mmol) was then added to the mixture, and the mixture was continued to heat at 65° C. for 2 hours. The mixture was cooled to room temperature, and 318 mg (1.32 mmol) copper nitrate trihydrate and 27 mg (0.27 mmol) acetic anhydride (a molar ratio of copper nitrate trihydrate and acetic anhydride being 5:1) were added to the mixture under an ice water bath. The mixture was stirred under the ice water bath for 30 minutes. The reaction was monitored by thin layer chromatography. When the reaction was complete, the solvent in the mixture was removed under reduced pressure. The mixture was then filtered, washed with ethanol to give a crude product. The crude product was recrystallized in 50 mL ethanol to give 85.3 mg (0.45 mmol) 6-chloro-5-nitro-2,4-diaminopyrimidine, a yield of 43.2%.

EXAMPLE 8

Preparation of 6-chloro-5-nitro-2,4-diaminopyrimidine

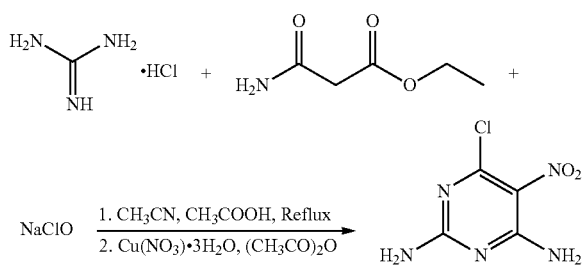

A mixture of 80 mg (0.84 mmol) guanidine hydrochloride, 132.4 mg (1.01 mmol) ethyl carbamoylacetate (a molar ratio of guanidine hydrochloride and ethyl carbamoylacetate being 1:1.2), and 100 mL acetonitrile was added to a 250 mL flask. Acetic acid was added slowly to the mixture to a pH of about 5 under stirring, and the mixture was heated at 65° C. for 12 hours. 29 mg NaClO (0.40 mmol) was then added to the mixture, and the mixture was continued to heat at 65° C. for 2 hours. The mixture was cooled to room temperature, and 251 mg (1.04 mmol) copper nitrate trihydrate and 21 mg (0.21 mmol) acetic anhydride (a molar ratio of copper nitrate trihydrate and acetic anhydride being 5:1) were added to the mixture under an ice water bath. The mixture was stirred under the ice water bath for 30 minutes. The reaction was monitored by thin layer chromatography. When the reaction was complete, the solvent in the mixture was removed under reduced pressure. The mixture was then filtered, washed with ethanol to give a crude product. The crude product was recrystallized in 40 mL ethanol to give 64.5 mg (0.34 mmol) 6-chloro-5-nitro-2,4-diaminopyrimidine, a yield of 40.1%.

EXAMPLE 9

Preparation of 6-chloro-5-nitro-2,4-diaminopyrimidine

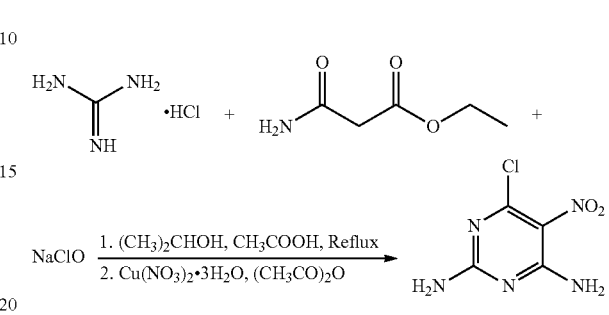

A mixture of 100 mg (1.04 mmol) guanidine hydrochloride, 164 mg (1.25 mmol) ethyl carbamoylacetate (a molar ratio of guanidine hydrochloride and ethyl carbamoylacetate being 1:1.2), and 45 mL isopropanol was added to a 250 mL flask. Acetic acid was added slowly to the mixture to a pH of about 5 under stirring, and the mixture was heated at 65° C. for 12 hours. 37 mg NaClO (0.50 mmol) was then added to the mixture, and the mixture was continued to heat at 65° C. for 2 hours. The mixture was cooled to room temperature, and 318 mg (1.32 mmol) copper nitrate trihydrate and 27 mg (0.27 mmol) acetic anhydride (a molar ratio of copper nitrate trihydrate and acetic anhydride being 5:1) were added to the mixture under an ice water bath. The mixture was stirred under the ice water bath for 30 minutes. The reaction was monitored by thin layer chromatography. When the reaction was complete, the solvent in the mixture was removed under reduced pressure. The mixture was then filtered, washed with ethanol to give a crude product. The crude product was recrystallized in 50 mL ethanol to give 79.6 mg (0.42 mmol) 6-chloro-5-nitro-2,4-diaminopyrimidine, a yield of 40.8%.

EXAMPLE 10

Measuring the Inhibitory Effect of 6-Chloro-5-Nitro-2,4-Diaminopyrimidine on the Growth of Six Leukemia Cells by CCK8 Assay Cell lines: HL-60 (acute myeloid leukemia), Jurkat (acute T cell leukemia), K562 (chronic myeloid leukemia), EOL-1 (human eosinophil leukemia), Dami (human megakaryocytic leukemia), 6T-CEM (human T cell leukemia) were provided by the Affiliated Hospital of Guangdong Medical College. The cells were cultured in RPMI1640 medium containing 10% fetal bovine serum, penicillin 100 U/mL, streptomycin 100 mg/L, at 37° C., 5% $CO_2$, and saturated humidity, in incubator, and logarithmic growth phase cells were used for experiments.

Test compounds: Imatinib solution and 6-chloro-5-nitro-2,4-diaminopyrimidine solution were prepared with physiological saline, and the final concentrations of the compounds were 1, 5, 10, 50, and 100 μmol/L.

Test method: Take the logarithmic growth leukemia cell lines, count, and inoculate at a density of $1 \times 10^5$/mL in a 96-well culture plate, 100 μL per well. After 24 hours of culture, 100 μL medium containing the different concentrations (double the target/final concentration) of compounds was added to each well. The medium containing the highest concentration of DMSO was used as a control. After 48 hours, 20 µL of CCK8 coloring solution was added to each well, the color was developed at 37° C., and OD450 was measured with a microplate reader until the absorbance was about 1.5. The inhibition rate was calculated by the following formula.

Inhibition Rate (%)=(1−absorbance of the test compound/absorbance of the control)×100%

The results are shown in Tables 1 and 2.

TABLE 1

Imatinib inhibits six leukemia cell lines

| Cell Lines | Imatinib Inhibition Rate % (X ± SD, n = 5) | | | | |
|---|---|---|---|---|---|
| | 1 µmol/L | 5 µmol/L | 10 µmol/L | 50 µmol/L | 100 µmol/L |
| K-562 | 66.41 ± 0.24 | 67.86 ± 0.14 | 71.56 ± 0.06 | 83.10 ± 0.18 | 88.33 ± 0.19 |
| HL-60 | 62.23 ± 0.13 | 69.54 ± 0.21 | 64.61 ± 0.24 | 83.12 ± 0.12 | 84.53 ± 0.35 |
| Jurkat | 66.73 ± 0.14 | 71.01 ± 0.11 | 73.29 ± 0.16 | 85.67 ± 0.20 | 90.88 ± 0.27 |
| EOL-1 | 63.56 ± 0.04 | 66.25 ± 0.24 | 68.37 ± 0.19 | 79.06 ± 0.29 | 86.40 ± 0.38 |
| Dami | 61.28 ± 0.11 | 65.38 ± 0.17 | 69.33 ± 0.18 | 82.11 ± 0.14 | 89.36 ± 0.45 |
| 6T-CEM | 68.16 ± 0.17 | 70.81 ± 0.12 | 74.90 ± 0.25 | 86.49 ± 0.16 | 91.30 ± 0.20 |

TABLE 2

6-Chloro-5-nitro-2,4-diaminopyrimidine inhibits six leukemia cell lines

| Cell Lines | 6-Chloro-5-nitro-2,4-diaminopyrimidine Inhibition Rate % (X ± SD, n = 5) | | | | |
|---|---|---|---|---|---|
| | 1 µmol/L | 5 µmol/L | 10 µmol/L | 50 µmol/L | 100 µmol/L |
| K-562 | 45.53 ± 0.08 | 61.51 ± 0.13 | 76.79 ± 0.11 | 77.30 ± 0.24 | 78.42 ± 0.16 |
| HL-60 | 3.87 ± 0.14 | −1.12 ± 0.17 | −7.66 ± 0.06 | −9.26 ± 0.17 | −14.17 ± 0.22 |
| Jurkat | −13.47 ± 0.21 | −15.92 ± 0.26 | −27.02 ± 0.19 | −28.10 ± 0.17 | −30.01 ± 0.20 |
| EOL-1 | −22.42 ± 0.15 | −22.99 ± 0.23 | −23.32 ± 0.16 | −19.33 ± 0.24 | −18.91 ± 0.33 |
| Dami | −14.21 ± 0.11 | −17.73 ± 0.19 | −22.01 ± 0.23 | −26.01 ± 0.14 | −30.27 ± 0.21 |
| 6T-CEM | −17.52 ± 0.16 | −21.05 ± 0.13 | −25.51 ± 0.14 | −28.13 ± 0.21 | −31.04 ± 0.13 |

The experimental results showed that the inhibitory effects of 6-chloro-5-nitro-2,4-diaminopyrimidine on the six leukemia cell lines tested varied greatly. 6-Chloro-5-nitro-2,4-diaminopyrimidine does not show any inhibition on HL-60, Jurkat, EOL-1, Dami, and 6T-CEM. But 6-Chloro-5-nitro-2,4-diaminopyrimidine exhibits a good inhibitory effect on the K-562 cell line. Specifically, the inhibition rate of 6-Chloro-5-nitro-2,4-diaminopyrimidine at 10 µmol/L exceeds that of imatinib. Therefore, 6-chloro-5-nitro-2,4-diaminopyrimidine selectively inhibits chronic myelogenous leukemia cell line.

EXAMPLE 11

Inhibition Test of Nude Mice Inoculated with K-562 Cell Line

Test compounds: 6-chloro-5-nitro-2,4-diaminopyrimidine and imatinib dissolved in normal saline.
Administration route: intraperitoneal injection (ip).
Test animals: nude mice, SPF level.
Cell line: chronic myeloid leukemia cell line K-562, from the Affiliated Hospital of Guangdong Medical College
Test method: 50 nude mice weighing 18-22 grams, both male and female. The K-562 cell was diluted to a final concentration of 10 million cells/mL for leukemia cells; each mouse was inoculated subcutaneously with 0.2 mL (containing 200 million leukemia cells). On the next day, the mice were randomly divided to 5 groups: 6-chloro-5-nitro-2,4-diaminopyrimidine group (dose: 3 mg/kg), 6-chloro-5-nitro-2,4-diaminopyrimidine group (dose: 8 mg/kg), 6-chloro-5-nitro-2,4-diaminopyrimidine group (dose: 20 mg/kg), positive control group (imatinib, 8 mg/kg) and blank control group. The 6-chloro-5-nitro-2,4-diaminopyrimidine groups and the positive control group were administered once a day for 7 consecutive days; the blank control group was given a corresponding volume of NS liquid. No test compounds were given for one day after the last dose. Animals were sacrificed by cervical dislocation, and weighed and dissected to weigh. The tumor weights were calculated for each group. The leukemia inhibition rate was calculated according to the following formula.

Tumor inhibition rate=(mean tumor weight in the control group−average tumor weight in the administration group)/mean tumor weight in the control group×100%, The results are show in Table 3 below.

TABLE 3

Imatinib and 6-chloro-5-nitro-2,4-diaminopyrimidine inhibit K-562 leukemia in mice

| Groups | Dosage (mg/kg) | Route of admin. × times | Number of mice before and after | Mouse weight before and after | Tumor weight (X ± SE) | Inhibition (%) |
|---|---|---|---|---|---|---|
| Control | | | 10/10 | 19.5/29.7 | 3.58 ± 0.28 | |
| Imatinib | 8 | ip × 7 | 10/10 | 19.5/20.4 | 0.93 ± 0.34 | 74.02 |
| 6-chloro-5-nitro-2,4-diaminopyrimidine | 3 | ip × 7 | 10/10 | 19.5/21.6 | 1.84 ± 0.26 | 48.41 |
| 6-chloro-5-nitro-2,4-diaminopyrimidine | 8 | ip × 7 | 10/10 | 19.5/26.7 | 0.87 ± 0.21 | 75.18 |
| 6-chloro-5-nitro-2,4-diaminopyrimidine | 20 | ip × 7 | 10/9 | 19.5/20.3 | 0.74 ± 0.23 | 79.34 |

As shown in Table 3, 6-chloro-5-nitro-2,4-diaminopyrimidine at 8 mg/kg has a leukemia inhibition rate of 75.18% in node mice. Further, there was no significant weight loss after administering 6-chloro-5-nitro-2,4-diaminopyrimidine at 8 mg/kg. This indicates that there is no obvious toxicity for 6-chloro-5-nitro-2,4-diaminopyrimidine at 8 mg/kg.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:
1. A method of preparing 6-chloro-5-nitro-2,4-diaminopyrimidine comprising:

reacting guanidine hydrochloride with ethyl carbamoylacetate and sodium hypochlorite in the presence of a metal nitrate salt and acetate anhydride in an organic solvent,

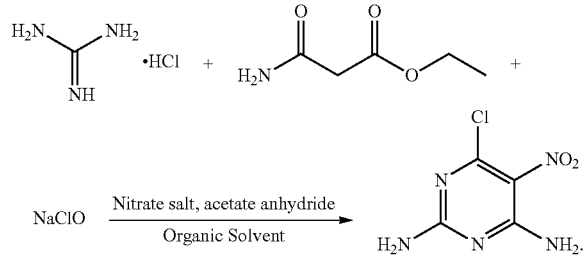

2. The method of claim 1, wherein the reaction of guanidine hydrochloride, ethyl carbamoylacetate, and sodium hypochlorite is a one pot reaction.

3. The method of claim 1, wherein the reaction of guanidine hydrochloride, ethyl carbamoylacetate, and sodium hypochlorite comprises the following steps:
(1) adding an acidic agent to a mixture of guanidine hydrochloride and ethyl carbamoylacetate in the organic solvent to a pH of 5.0-5.5, heating the mixture to 60-80° C. for 10-12 hours;
(2) adding sodium hypochlorite to the mixture, continuing heating the mixture to 60-80° C. for 2-3 hours; the
(3) cooling the mixture to room temperature, adding the metal nitrate salt and acetate anhydride to the mixture in the presence of an ice water cooling bath, stirring the mixture for 30-40 minutes;
(4) cooling the mixture to room temperature, removing the solvent, filtering, washing with ethanol to obtain crude 6-chloro-5-nitro-2,4-diaminopyrimidine; and
(5) recrystallizing the crude 6-chloro-5-nitro-2,4-diaminopyrimidine in ethanol to obtain 6-chloro-5-nitro-2,4-diaminopyrimidine.

4. The method of claim 1, wherein the metal nitrate salt is potassium nitrate or copper nitrate trihydrate.

5. The method of claim 1, wherein the organic solvent is ethanol, acetonitrile, or isopropanol.

6. The method of claim 5, wherein the organic solvent is ethanol.

7. The method of claim 1, wherein the molar ratio of guanidine hydrochloride and ethyl carbamoylacetate is 1:1-1:1.5.

8. The method of claim 7, wherein the molar ratio of guanidine hydrochloride and ethyl carbamoylacetate is 1:1.2.

9. The method of claim 3, wherein the acidic agent is $ZnCl_2$, $AlCl_3$, HCl, or acetic acid.

10. The method of claim 9, wherein the acidic agent is acetic acid.

11. The method of claim 3, wherein in step (2), the mixture is heated to 65° C. for 2 hours.

12. The method of claim 1, wherein the molar ratio of the metal nitrate salt and acetate anhydride is 5:1.

13. The method of claim 3, wherein in step (3), the mixture is stirred for 30 minutes.

* * * * *